(12) United States Patent
Havelange et al.

(10) Patent No.: US 8,368,043 B2
(45) Date of Patent: Feb. 5, 2013

(54) GANTRY ROLLING FLOOR

(75) Inventors: Yorick Havelange, Lonzée (BE);
Sëbastien De Neuter, Jandrenouille (BE); Vincent Piret, Gembloux (BE); Bernard Bleeckx, Perewez (BE)

(73) Assignee: Ion Beam Applications S.A., Louvain-la-Neuve (BE)

( * ) Notice: Subject to any disclaimer, the term of this patent is extended or adjusted under 35 U.S.C. 154(b) by 0 days.

(21) Appl. No.: 13/142,575

(22) PCT Filed: Dec. 22, 2009

(86) PCT No.: PCT/EP2009/067808
§ 371 (c)(1),
(2), (4) Date: Aug. 26, 2011

(87) PCT Pub. No.: WO2010/076270
PCT Pub. Date: Jul. 8, 2010

(65) Prior Publication Data
US 2011/0299657 A1 Dec. 8, 2011

(30) Foreign Application Priority Data

Dec. 31, 2008 (EP) .................................... 08022552
May 29, 2009 (EP) .................................... 09161605

(51) Int. Cl.
*A61N 5/10* (2006.01)
*A61B 6/04* (2006.01)

(52) U.S. Cl. ............... 250/505.1; 250/492.3; 250/492.1; 250/454.11; 378/65; 315/500; 315/502; 315/503; 315/505

(58) Field of Classification Search ............... 250/505.1, 250/454.11, 492.3, 492.1; 378/65; 315/500, 315/502, 503, 505
See application file for complete search history.

(56) References Cited

U.S. PATENT DOCUMENTS
(Continued)

FOREIGN PATENT DOCUMENTS
DE 10 2007 011 399 A1 9/2008
EP 1 402 923 A1 3/2004
(Continued)

OTHER PUBLICATIONS

International Search Report and Written Opinion of the International Searching Authority, International Patent Application No. PCT/EP2009/067808, date of the actual completion of the international search Apr. 27, 2010, 7 pages.

*Primary Examiner* — Nikita Wells
(74) *Attorney, Agent, or Firm* — Fitch, Even, Tabin & Flannery, LLP (57) ABSTRACT

The present invention relates to an irradiation unit for emitting a particle beam, a gantry including the irradiation unit, a squirrel cage structure located within and supported by the gantry, a frame arranged so as to be motionless, a moving floor including a plurality of elongated members forming a primary caterpillar, two moving floor guide units having a truncated circle shape, facing each other, attached to said squirrel cage structure and the motionless frame, respectively. Each of the two moving floor guide units includes at least a first rail, said the primary caterpillar being slidably arranged on the first rail. Each moving floor guide unit includes at least a second rail having a truncated circle shape and the moving floor includes at least one secondary caterpillar including elongated members flexibly connected to each other.

17 Claims, 7 Drawing Sheets

U.S. PATENT DOCUMENTS

| | | | |
|---|---|---|---|
| 5,993,373 A * | 11/1999 | Nonaka et al. | 600/1 |
| 6,803,591 B2 * | 10/2004 | Muramatsu et al. | 250/492.3 |
| 7,030,396 B2 * | 4/2006 | Muramatsu et al. | 250/492.3 |
| 7,345,291 B2 * | 3/2008 | Kats | 250/492.22 |

FOREIGN PATENT DOCUMENTS

| | | |
|---|---|---|
| EP | 1 967 230 A1 | 9/2008 |
| JP | 2001353228 A | 12/2001 |
| WO | 2006/076545 A2 | 7/2006 |

* cited by examiner

4a(i) normal situation     4a(ii) blocking situation

4b(i) normal situation     4b(ii) blocking situation

GANTRY ROLLING FLOOR

CROSS REFERENCE TO RELATED APPLICATIONS

This application is a national phase application of International Application No. PCT/EP2009/067808, filed Dec. 22, 2009, designating the United States and claiming priority to European Patent Application No. 08022552.7, filed Dec. 31, 2008, and European Patent Application No. 09161605.2, filed May 29, 2009, all of which are incorporated by reference herein in their entirety.

TECHNICAL FIELD

The present invention is related to a medical apparatus for particle therapy wherein an irradiation unit is able to move inside a patient enclosure together with an imaging device.

STATE OF THE ART

Conventional cancer therapy uses high energetic photons like X-rays or gamma rays to destroy tumour cells. The main drawback of that method is that healthy cells surrounding tumour cells are irradiated in the same time, damaging these healthy cells which may cause atrophy or several secondary effects, such as the release of secondary tumours. Moreover, conventional radiotherapy often needs relatively high energy doses to reach and destroy deep tumours, since the photon energy traversing tissues is rapidly absorbed.

Particle therapy or more particularly hadron therapy is a growing field in cancer therapy and is particularly appropriate in situations where conventional radiotherapy constitutes a risk for the patient. Hadrons (i.e. neutrons, protons, pions, ions such as carbon ions) have physical advantages with respect to X-rays or gamma rays in the radiotherapy fields. Protons of a given energy, i.e. forming a mono-energetic proton beam, have a defined range and do not penetrate beyond that range. Furthermore, they deposit their maximum dose in the so-called Bragg Peak, which corresponds to the point of greatest penetration of the radiation in a target volume. Because the Bragg peak position depends on the energy of the hadron beam, it is evident that by precisely controlling and modifying the energy, one can place the Bragg Peak at a suited depth in the body corresponding to the position of a tumour so as to administer the greatest radiation energy to that point and spare, by contrast, healthy tissue surrounding said tumour. Moreover, by combining several mono-energetic proton beams of different energies (i.e. performing the range modulation) it is possible to extend the Bragg Peak region in order to match the thickness of the tumour and irradiate the target with a uniform dose while controlling the dose load on surrounding healthy tissue and organs.

Typically, a hadron therapy device comprises firstly a particle accelerator (e.g. a cyclotron, a synchrotron, a linac) that generates an accelerated hadron beam having a desired energy value. It comprises secondly a beam transport line guiding the hadron beam from the particle accelerator to a target, said hadron beam passing trough a nozzle located at the exit of the beam transport line and before the target. The nozzle drives and shapes the hadron beam towards a specific target. In basic systems, only a stationary nozzle is provided.

As tumours can take many variable three-dimensional forms, it is suitable to irradiate them with different angles of incidence in order to have the more precise targeting of the tumour and to avoid damages to healthy tissues. Such a targeting is made possible by the means of a rotating irradiation device such as a rotating gantry supporting a beam transport line provided by deflecting means and a nozzle.

Furthermore, patient positioning is of particular importance for matching, as much as possible, the shape, size and location of the tumour. A positioning fulfilling these requirements is allowed by a patient enclosure, located in a rotating gantry, the patient enclosure comprising a horizontal floor permitting the practitioner to accurately position the patient and some imaging devices for monitoring patient positioning.

A rotating radiation chamber for radiation therapy is described in U.S. Pat. No. 5,993,373. This rotating radiation chamber comprises an irradiation unit, also called nozzle, two semi-circular moving ring rails and a fixed ring rail sandwiching a moving floor having a horizontal section. Said moving floor is provided with an opening for the nozzle and is moved in synchrony with the nozzle while a motor as driving means rotates the moving ring rail in the reverse direction. Monitoring means of the moving ring rail position with respect to the fixed ring rail are also provided. If the position of the moving ring rail differs from the fixed ring rail, the apparatus is stopped to avoid breaking of the moving floor. In such a rotating chamber, the moving floor covers almost the entire surface except for the region close to the radiation beam irradiating section (the nozzle) of rotation gantry. This configuration may give a feeling of insecurity to the patient.

Another design of such a rotating radiation chamber is described in U.S. Pat. No. 6,803,591. The device comprises an annular frame located within and supported by the gantry and synchronised with a second annular frame fixedly located opposite to the first annular frame. Both annular frames comprise on their respective opposed sides ring guide portions in which guide grooves are formed. The guide grooves are semi-cylindrical in shape and sandwich a moving floor in order to give to the moving floor a horizontal section. Synchronization between annular frames is ensured by an anti-corotation system instead of a motor rotating the moving annular frame of U.S. Pat. No. 5,993,373. The anti-corotation system has a pair of sprockets coupled with a connecting shaft and is provided on the inside of the rotary shell (the gantry). Sprockets of the anti-corotation means meshes with a conveyor chain disposed on each of the annular frames. In case of blocking or derailment of a sprocket, such a device could be seriously damaged. Other mechanical parts are present close to the nozzle as telescopic cylinders coupling the extremities of the moving floor with the nozzle. These telescopic cylinders are able to retract or extend themselves in order to cover the horizontal floor section with the moving floor. Nevertheless, there still appears a gap between the nozzle and the moving floor in the area where the telescopic cylinder is extended.

Application DE 10 2007 011 399 discloses a particle therapy system comprising a gantry supporting a movable floor segment. Said movable floor segment is supported on the side wall of the gantry using rolling bearings, so the movable floor segment can stay in a horizontal position while the gantry rotates. The nozzle and the movable segment floor comprise resilient buffer elements on their both sides in order to avoid hard impact between them when the irradiation angle is oriented from below. In this case, the nozzle can push the movable floor segment which rotates then together with the gantry. It is possible to dispose an imaging device for the patient position monitoring on this movable floor segment, but when the irradiation occurs at an angle oriented from below, the movable floor segment may be strongly inclined that obstructs the access in the radiation chamber for patient repositioning.

Document WO2006/076545 discloses an automatic retractable floor plant for a rotating gantry. The plant comprises a carriage assembly slidably supported within the gantry to maintain a substantially constant orientation while the gantry is rotating. The carriage assembly is constituted by a plurality of extendable/retractable panels sliding over correspondent non movable panels fixed on the carriage assembly. The movable panel's sizes are matched to cover the distance between the carriage assembly and the fixed floor of the treatment room. Each movable panel has a flat surface able to support a person. Nevertheless, such a plant is not esthetic since almost all the inside of the gantry is visible, which may give a feeling of fear to the patient. Also, one or more movable panel could block itself and collide with the nozzle as said nozzle rotates during the treatment. For this reason, a control system for each panel is needed which complicates the overall system.

Document JP2001-353228 discloses a hadron therapy apparatus comprising a moving floor in a rotatable gantry. The moving floor is a caterpillar divided in three portions A, B, C. The apparatus comprises two ring rails having a circle truncated shape to provide the moving floor:
 a first ring rail held by a fixed support to a ceiling and a floor of the building, and;
 a second ring rail held by a fixed support to the rear surface panel which stops the depth size of a medical treatment gauge.

Both rails sandwich the moving floor, and allow the rotation of the moving floor with the gantry. Caterpillar C is able to enter in contact with caterpillar A and B, therefore the three caterpillars slide necessarily into the same rails. Caterpillar C is fixed to the body of the gantry by a latch implement and is able to slide into the two said ring rails. A first extremity of caterpillar A and caterpillar B are attached to an irradiation unit. A first cover rolling up machine is fixed to the second extremity of caterpillar A and to a first extremity of caterpillar C, the said first extremity of caterpillar A and the said first extremity of caterpillar C facing each other. A second cover rolling up machine is fixed to the second extremity of caterpillar B and to the second extremity of caterpillar C, the said second extremity of caterpillar B and the said second extremity of caterpillar C facing each other. For example, when the first extremity of caterpillar C is against the second extremity of caterpillar A, the cover is rolled into the cover rolling-up machine and there is a space between the second extremity of caterpillar B and the second extremity of caterpillar C which is filled by the unrolled cover of the second cover rolling up machine. The covers have the drawback to provide a flexible frame between the spaces created comprised between the caterpillars. Moreover a blocking of a rolling up machine can occur during the rolling up or the unrolling of the cover which can damage this cover or the fixation of the caterpillars.

AIMS OF THE INVENTION

The present invention aims to provide a particle therapy apparatus which does not have the drawbacks of prior art.

In particular, it is an aim of the present invention to provide a particle therapy apparatus comprising a patient enclosure having a flat floor accessible to the practitioner without gaps or weaker parts close to the irradiation unit for any irradiation angle.

It is a further aim of the present invention to provide such a particle therapy apparatus able to comprise imaging devices.

Finally, It is a further aim of the present invention to provide an efficient particle therapy apparatus having a high safety level wherein minimal damage occurs in case of blocking of a part of the apparatus.

SUMMARY OF THE INVENTION

The present invention relates to an apparatus for particle therapy in a treatment room as disclosed in the appended claims. The apparatus according to the invention comprises
 an irradiation unit for emitting a particle beam,
 a gantry comprising the irradiation unit, said gantry being rotatable around an axis,
 a squirrel cage structure, located within and supported by said gantry so that it can rotate relative to said gantry around said axis,
 a frame arranged so as to be motionless (immobile) and fixed to a wall of the treatment room,
 a moving floor comprising a plurality of elongated members flexibly connected to each other and forming a primary caterpillar,
 two moving floor guide unit having a truncated circle shape, facing each other, attached to the squirrel cage structure and the motionless frame respectively, and each of the two moving floor guide unit comprising at least a first rail,
and wherein each moving floor guide unit further comprises at least a second rail having a truncated circle shape and the moving floor further comprises at least one secondary caterpillar comprising elongated members flexibly connected to each other by linking means, slidably arranged on said second rails and attached to the irradiation unit so that it can rotate with the irradiation unit.

Preferably, a set of second rails is positioned externally relatively to the first rails.

Preferably, a set of second rails is positioned internally relatively to the set of first rails.

Preferably, said irradiation unit comprises two pairs of guiding units connected to said irradiation unit, each secondary caterpillar comprising at least a pivot connected to the closest end of said caterpillar relatively to the irradiation unit and said pivots being arranged so as to slide into said guiding units.

Preferably, the apparatus for particle therapy according to the present invention further comprises a telescopic arm connected to both said gantry and said primary caterpillar.

Preferably, the elongated members comprise wood, plastic, glass fiber, composite material, metal such as iron, steel, aluminium, magnesium, titanium, copper nickel, zinc or a combination thereof.

Preferably, the elongated members comprise aluminium.

Preferably, the irradiation unit further comprises a first X-ray beam generator.

Preferably, the apparatus according to the present invention comprises a second X-ray beam generator connected to said gantry, located beside said telescopic arm, the directions of the X-ray beams delivered by the first and second X-ray beam generators being orthogonal.

Preferably, the apparatus according to the present invention comprises moving floor monitoring means for monitoring the movements of the moving floor.

Preferably, the apparatus according to the present invention comprises gantry control means for controlling the movements of the gantry.

Preferably, the apparatus according to the present invention comprises security means to avoid damaging the apparatus. In an apparatus wherein said irradiation unit comprises two pairs of guiding units connected to said irradiation unit, each secondary caterpillar comprising at least a pivot connected to the closest end of said caterpillar relatively to the irradiation unit and said pivots being arranged so as to slide into said guiding units, said security means may be buffer means, wherein the guiding units are connected to the irradiation unit through said buffer means arranged between each guiding unit and the irradiation unit. Said buffer means may comprise piston and cylinder arrangements.

Preferably, said security means are adapted to absorb a circular motion of the gantry of at least 5° for avoiding any damage to the irradiation unit.

Preferably, moving floor monitoring means provide information to the gantry control means and to said security means. Said moving floor monitoring means may comprise a load cell arranged on the telescopic arm, to check if the tensile strength between the caterpillar(s) and the gantry and/or between the caterpillar(s) and the telescopic arm does not exceed a predetermined value.

Preferably, the security means (401) are set on and/or set off accordingly to information received from said moving floor monitoring means.

BRIEF DESCRIPTION OF THE DRAWINGS

FIGS. 4a(i) and 4b(i) are examples of embodiments of the irradiation unit provided by the (buffer) security means inactivated in a normal situation and FIGS. 4a(ii) and 4b(ii) are the corresponding irradiation unit provided by the (buffer) security means activated in a situation of failure of a part of the hadron therapy system.

DETAILED DESCRIPTION OF THE PRESENT INVENTION

The present invention provides a particle therapy apparatus which does not have the drawbacks of prior art.

In the present invention, the term "particle therapy" is used in its broadest meaning which comprises therapy using ionizing radiation such as hadron therapy, radiotherapy using photons, electrons or any other type of particle.

In particular, the present invention provides a particle therapy apparatus comprising a patient enclosure having a flat floor accessible to the practitioner without gaps or weaker parts close to the irradiation unit for any irradiation angle.

Furthermore, the present invention provides such a particle therapy apparatus able to comprise imaging devices.

Finally, the present invention provides an efficient particle therapy apparatus having a high safety level wherein minimal damages occur in case of blocking of a part of the device or apparatus.

Figure 1A:
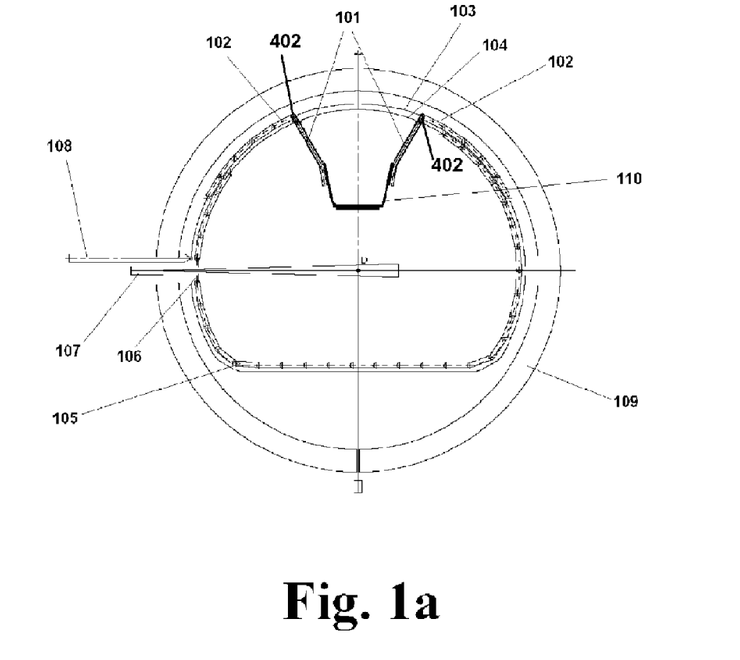
FIG. 1a-c are simplified front views of a hadron therapy system gantry, comprising a patient enclosure, the patient enclosure comprising an irradiation unit.
Figure 1B:
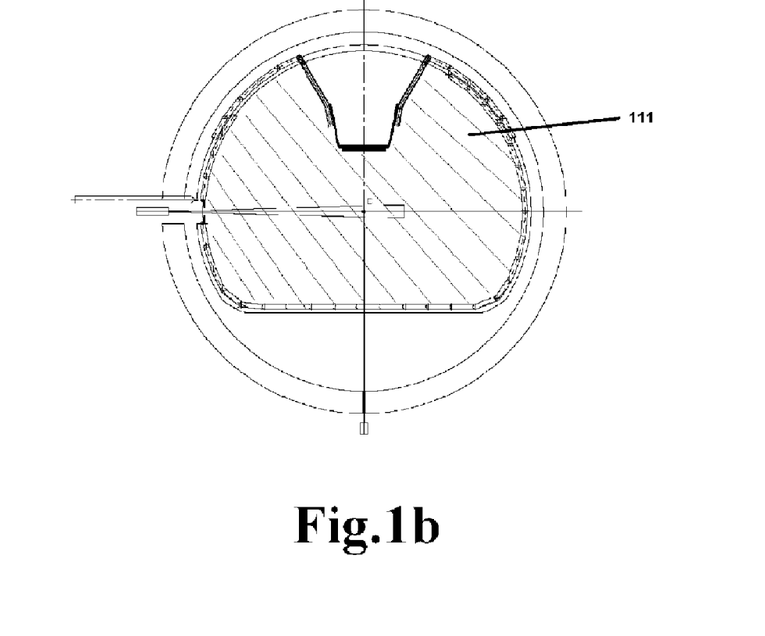
Figure 1C:
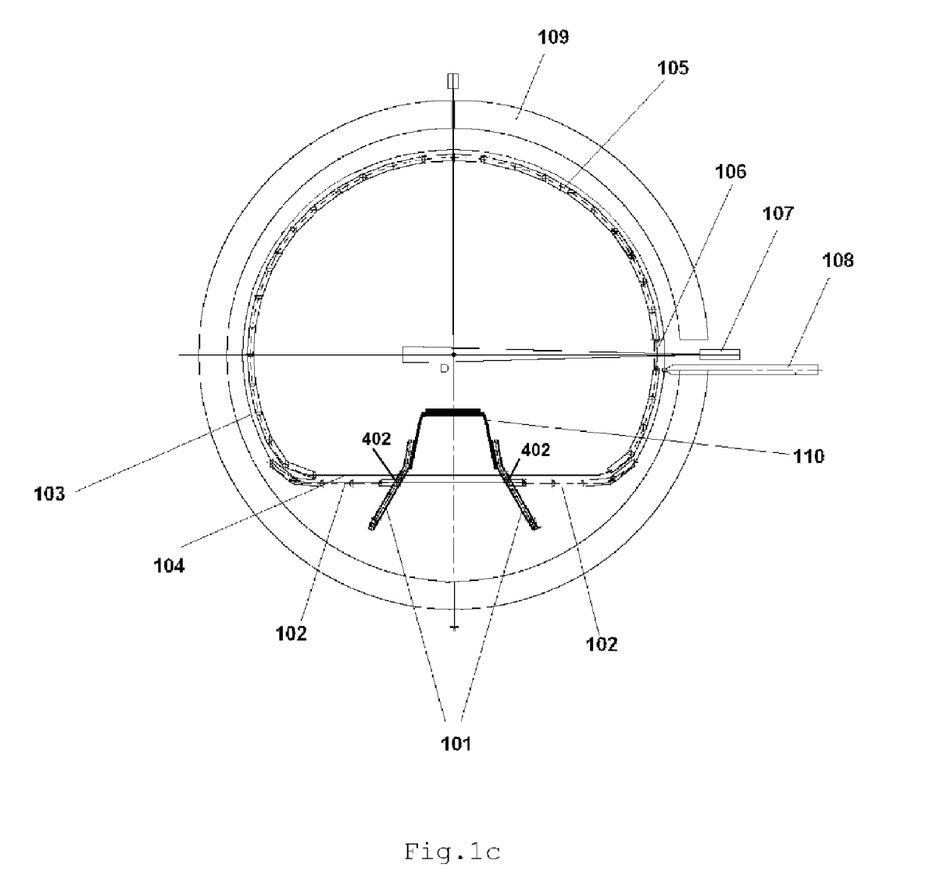
Figure 2:
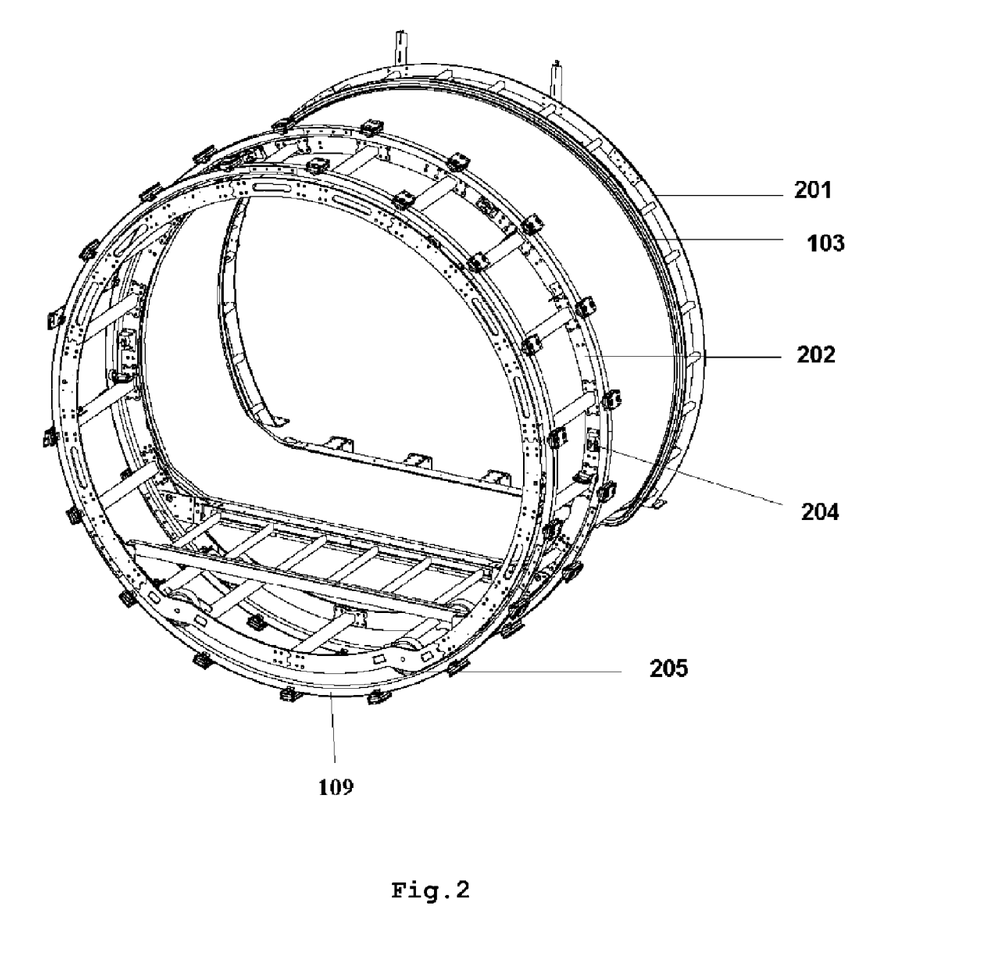
FIG. 2 is a perspective back view of a part of the gantry comprising the patient enclosure. The caterpillar's plates are omitted for clarity.

A medical particle therapy apparatus is described referring to FIGS. 1 and 2. It comprises a charged particle beam generating unit such as a cyclotron or a linac (not represented) and a gantry 109.

A beam transport line guides the accelerated particle beam from the beam generating unit towards a target located in a patient enclosure located inside a rotating gantry.

The beam transport line comprises deflecting means, fits with the gantry and is able to rotate with the gantry.

FIG. 1 a-c show a front view of a part of a particle therapy apparatus, comprising a gantry 109 (represented partially on FIG. 1 and FIG. 2). Said gantry is able to rotate around an axis of rotation D, said axis being perpendicular to the plane of the drawing.

Preferably, said gantry comprises a beam support line (not shown) guiding the beam produced by a particle (hadron) accelerator through an irradiation unit 110, such as a nozzle, towards a target (e.g. a tumor) located in the patient enclosure 111, shown as a hatched zone in FIG. 1b, located in the gantry 109.

The irradiation unit 110 is attached to the gantry 109 and preferably rotates in synchrony with the gantry 109.

The hadron therapy apparatus further comprises a frame 201 fixed to the treatment room, later called motionless (immobile) frame.

Preferably, said patient enclosure 111 comprises the irradiation unit 110 and all panels and/or covers that visually finish and close a room environment inside the gantry.

A patient bed or couch (not represented) can be positioned from the outside into the patient enclosure 111.

Preferably, the patient enclosure 111 is designed to give a feeling of safety to the patient located inside this enclosure.

Figure 3:
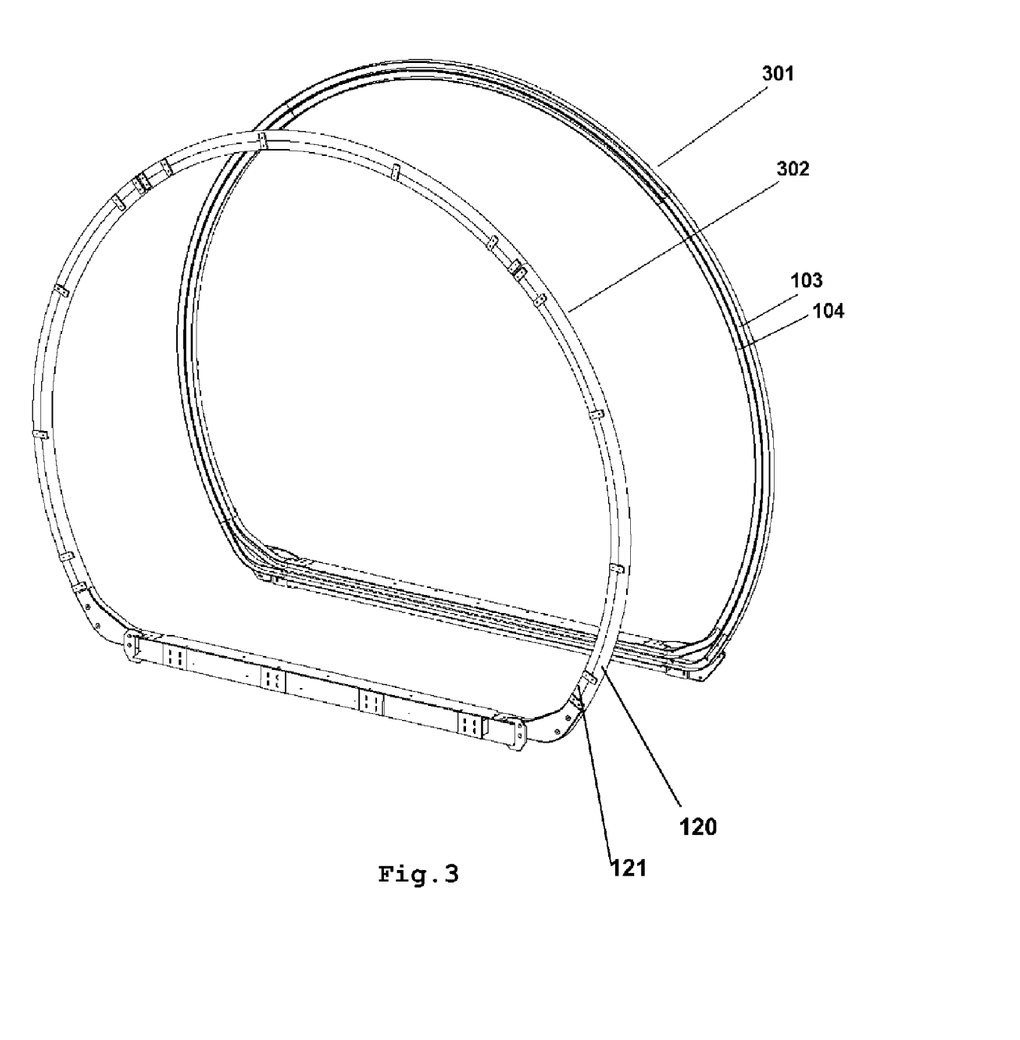
FIG. 3 is a front view of both double rails located within the gantry, i.e. front double rail and rear double rail.

Preferably, the patient enclosure 111 further comprises a moving floor located between two moving floor guide units: a front moving floor guide unit 301 and a rear moving floor guide unit 302 (FIG. 3).

The front moving floor guide unit 301 is attached to said motionless frame 201.

The front moving floor guide unit 301 comprises a front set of double rails 103,104 (FIG. 3).

The rear moving floor guide unit 302 is fixed to a squirrel cage structure 202.

The rear moving floor guide unit 302 comprises a rear set of double rails 120,121 (FIG. 3, backside of the rails is visible).

The rear and front moving floor guide units 301,302 are facing each other.

In the present invention, the term "squirrel cage structure" refers to a three dimensional frame adapted to provide a support for the moving floor(s).

More particularly, said three-dimensional frame is adapted to be embedded in the gantry.

The squirrel cage structure 202 comprises wheels 204,205 that enable the squirrel cage structure 202 to stay stationary during the rotation of the gantry 109.

The moving floor comprises at least one caterpillar (105 and/or 102).

Figure 5:
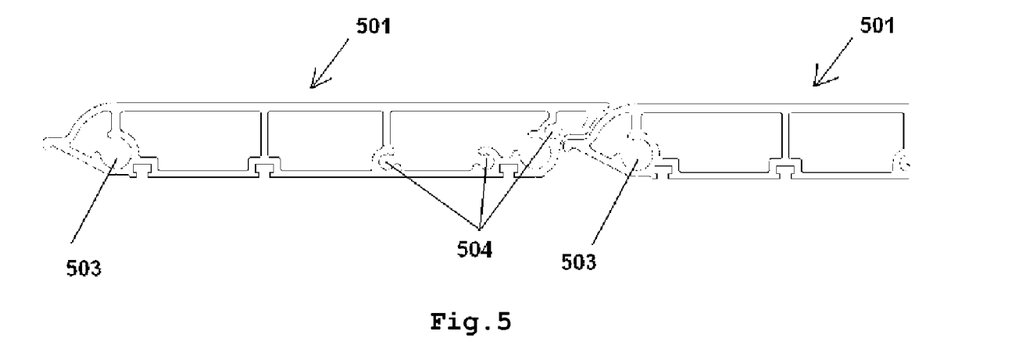
FIG. 5 is a lateral view of an example of elongated members of caterpillars according to the present invention.

A caterpillar comprises (or consist essentially of) an assembly of elongated members 501 attached to each other to form a moving floor (FIG. 5).

The caterpillar comprises means to allow the caterpillar to slide into the rails of the moving floor guide units, i.e. the elongated members move along the rails whilst remaining essentially perpendicular to said rails.

Figure 6:
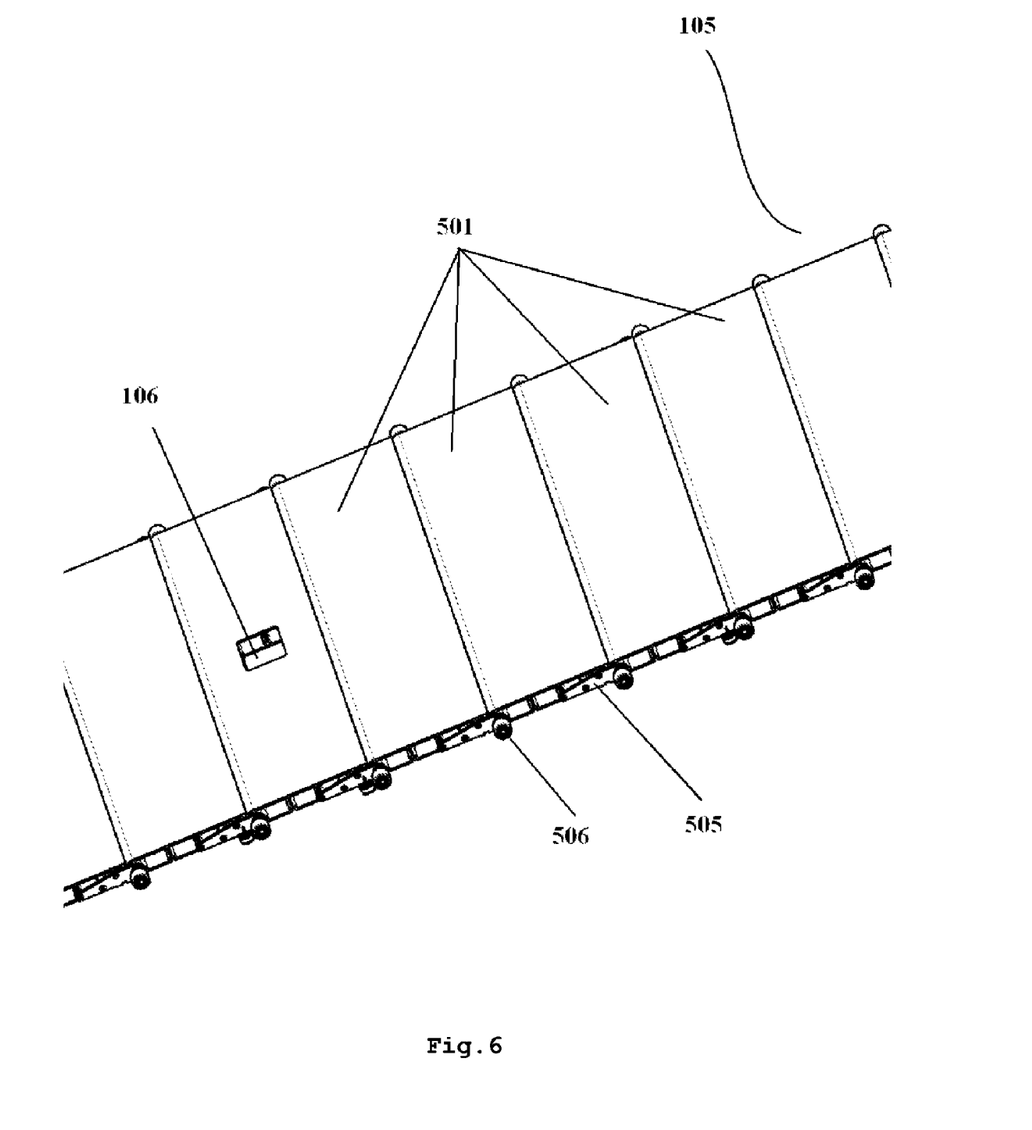
FIG. 6 is a top part view of elongated members linked together comprising wheels.

Preferably, these means are wheels 506 fixed on each elongated member 501 (FIG. 6).

Preferably, the moving floor comprises at least two caterpillars: a primary caterpillar 105 and at least one secondary caterpillar(s) 102 (FIG. 1a-c).

More preferably, the moving floor comprises a primary caterpillar 105 and two secondary caterpillars 102.

Preferably, the primary caterpillar 105 and the two secondary caterpillars 102 are adapted to slide into double rails of the moving floor guide units 301,302 and therefore to provide a horizontal floor in the patient enclosure whatever the position of the irradiation unit.

Preferably, each of the double rails 103,104 and 120,121 respectively, has a truncated circle shape (FIG. 3).

Said double rails comprise an external rail (103 for front floor guiding unit 301 and 120 for rear floor guiding unit 302) and an internal rail (104 for front floor guiding unit 301 and 121 for rear floor guiding unit 302).

One of the moving floor guide units 301 is fixed on the squirrel cage structure 202 while the other moving floor guide unit 302 is fixed on the motionless (immobile) frame 201.

Advantageously, in a view from the inside of the patient enclosure 111, the secondary caterpillars 102 are located backwards of (i.e. further away from the patient than) the primary caterpillar 105.

Preferably, said secondary caterpillars 102 slide into the external rails 103,120 of rear and front double rails and the primary caterpillar 105 slides into the internal rails 104,121 of the rear and front set of double rails.

Preferably, said elongated members 501 of the caterpillars comprise a rigid material such as wood, plastic, glass fiber, a composite material, a metal such as iron, steel, aluminum, magnesium, titanium, copper, nickel, zinc or a combination hereof.

More preferably, said elongated members comprise aluminium.

A preferred shape, but not limitative, for the elongated members of the caterpillar is shown at FIG. 5 and FIG. 6. A lateral view of two elongated members 501 is shown on FIG. 5.

Advantageously, elongated members have a hollowed structure for gain of weight and the shape of these elongated members confers them stiffness such that they enable to the caterpillars, being pulled mechanically, to maintain the squirrel cage structure in a fixed position and synchronized with the building-fixed frame.

Advantageously, elongated members 501 also comprise on their lateral sides cavities 503 for insertion of wheels 506 and cavities 504 for insertion of linking means 505.

More preferably said primary caterpillar 105 is pulled by a telescopic arm 108 fixed on the gantry 109 and slides in synchrony with the gantry 109 into internal rails 104 of both double rails.

Preferably the secondary caterpillars 102 slide into external rails 103 of the front set and the rear set of double rails.

Advantageously the secondary caterpillars 102 are pulled or pushed mechanically by the irradiation unit 110 and with the gantry 109.

The secondary caterpillars are thus attached at one of their ends to the irradiation unit, in such a way that the irradiation unit's rotation pushes one secondary caterpillar forward and pulls the other secondary caterpillar along.

As shown in FIG. 1*a-c*, the irradiation unit 110 preferably comprises two pairs of guiding units 101; for example parallel rails, each pair of parallel rails being disposed on both sides in both rotation directions of the irradiation unit.

Preferably, each elongated member 501 located at the closest extremity of a secondary caterpillar 102 relative to the irradiation unit 110 comprises at least one pivot 402 arranged to slide into (i.e. between) said parallel rails 101 of the irradiation unit 110, while the irradiation unit is pulling or pushing the secondary caterpillar(s) 102.

In other words: on each side of the irradiation unit 110, each lateral end of the last elongated member 501 of the secondary caterpillar 102 is pivotably arranged between the rails of a guiding unit 101, each guiding unit comprising a pair of rails.

The pivot 402 may be regarded as part of the secondary caterpillar or as part of the guiding units 101. According to an embodiment, the pivot 402 is brought into practice by providing on each lateral side of the last elongated member of the secondary caterpillar a rotating bearing supporting a rotating axis in a bearing housing, the rotating axis being connected to each side of said last elongated member 501 of the secondary caterpillar, and the bearing housing being movably supported by the rails 101, or vice versa: the rotating axis is movably supported by the rails 101 and the bearing housing is connected to the secondary caterpillar.

As shown in FIG. 1*c*, the sliding of the pivot 402 between the rails allows the secondary caterpillars to follow the truncated portion of the rails, when the irradiation unit is positioned in the angle range corresponding to said truncated portion. Each pair of double rails 101 must have a blocking means at the end, to ensure that the caterpillars remain between the rails, when the irradiation unit is positioned in the upper half of the patient enclosure (FIGS. 1*a* and 1*b*).

Preferably, as seen in FIG. 1, the ends of the primary caterpillar 105 overlap with the ends of the secondary caterpillars 102 which are not attached to the irradiation unit, so that the rolling floor does not have any gaps, regardless of the position of the irradiation unit.

The wheels 204,205 fixed to the squirrel cage structure 202 and the stiffness of the caterpillar assembly can prevent rotation of the squirrel cage structure, and therefore of the rear moving floor guide unit 302, even if the squirrel cage structure attempts to rotate together with the gantry during the rotation of the gantry.

Therefore, the position of the rear moving floor guide unit 302 and the front moving floor guide unit 301 which are located opposite to each other can be kept substantially unchanged even if the gantry rotates. Consequently, it is possible for the flexible moving floor to form a substantially level access floor regardless of the position of the irradiation unit.

Consequently the patient enclosure 111 has a safe rolling floor in which the irradiation unit 110 is able to rotate freely, able to support one person or more, even if the irradiation unit 110 is located at the level floor of patient enclosure 111 since no gaps or weaker parts around the irradiation unit are present.

Preferably, the gantry comprises gantry control means for controlling the movements of the gantry.

More preferably, the apparatus comprises a moving floor monitoring means for monitoring the movements of the moving floor.

In case of a failure detected by the moving floor monitoring means, the moving floor monitoring means sends the information for stopping the movement of the gantry in emergency to the gantry control means.

More preferably, the apparatus comprises security means which are activated in case of a failure detected by the moving floor monitoring means.

As the gantry is an imposing device having defined inertia, therefore it is not possible to stop the gantry in an abrupt way without damaging it.

During the stopping phase, the gantry decelerates first, and is able to stop after a circular motion of maximum 5°, and preferably less than 3°.

Preferably, security means are located on the irradiation unit 110 to avoid any damage to irradiation unit 110 in case of blocking of one of the caterpillars.

Preferably, the security means on the irradiation unit 110 are buffer means 401.

Figure 4:
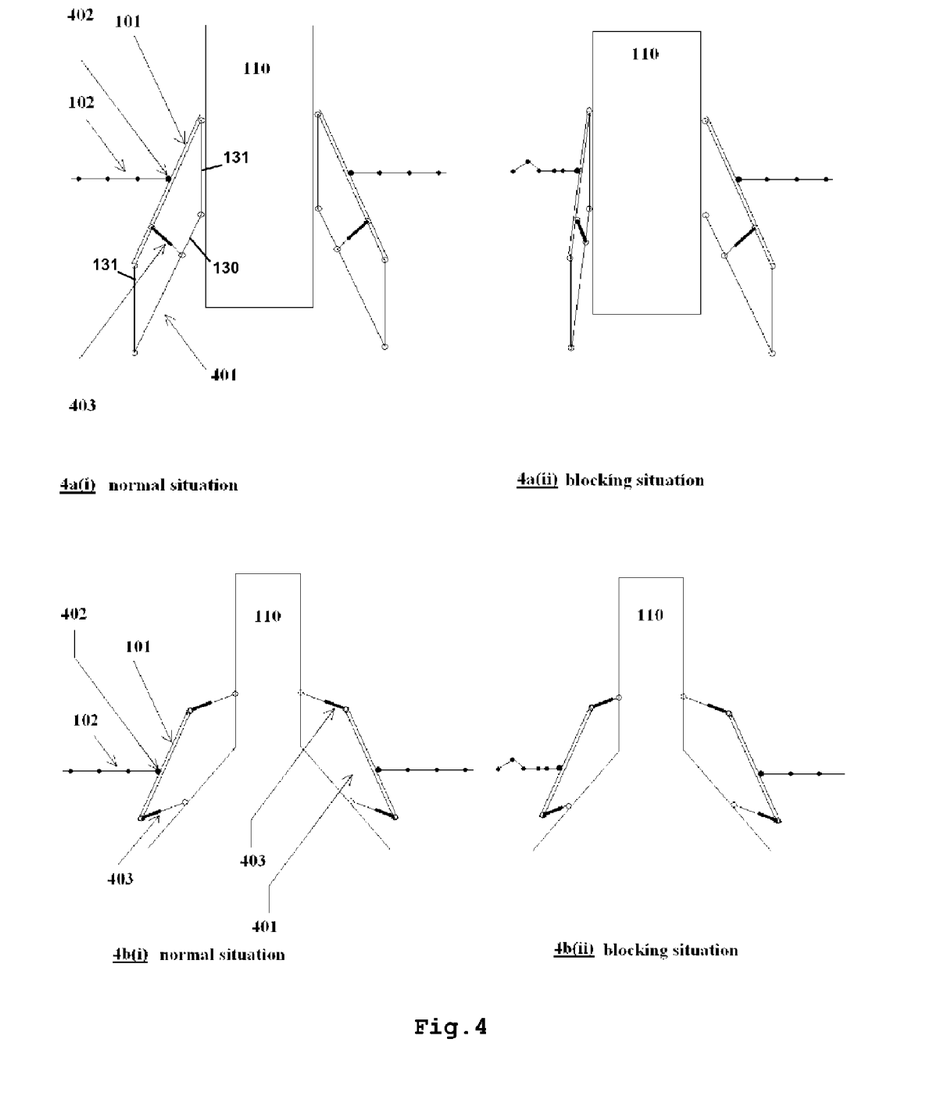

FIG. 4 shows examples of embodiments of buffer means according to the present invention, wherein a buffer means comprising pistons 403 located between the irradiation unit 110 and the guiding units 101 is described. Pistons 403 may comprise a load cell as moving floor monitoring means and are able to contract or retract when the tensile strength on said pistons 403 exceeds a predetermined value.

In case of blocking of a caterpillar, the secondary caterpillar(s) could be in contact with the irradiation unit and damage it because caterpillar's plates are rigid.

To absorb the impact between the irradiation unit and the caterpillar(s), the buffer means 401, having for example a parallelogram shape, act as a shock absorber, thereby avoiding any damage to the irradiation unit during the stopping phase.

FIG. 4a shows an embodiment, wherein each double rail 101 is pivotably arranged with respect to the irradiation unit, and wherein a buffer means is present between the double rail and a parallel beam 130 forming a deformable parallelogram along with the double rail and two additional beams 131. The buffer means may comprise a piston and cylinder arrangement 403. In this case, when the caterpillar malfunctions (FIG. 4a(ii)), the parallelogram folds and the double rails 101 rotate with respect to the irradiation unit.

In the embodiment of FIG. 4b, the ends of the double rails 101 are connected to the irradiation unit through pistons/cylinder arrangements having a fixed orientation, i.e. when the caterpillar malfunctions (FIG. 4b(ii)), the double rail moves with respect to the irradiation unit, whilst maintaining a fixed orientation.

These buffer means are designed to absorb a circular motion of at least 5°.

The vertical bottom (i.e. the vertical wall) of the squirrel cage structure, i.e. the vertical bottom of the patient enclosure, ends by a back wall panel which makes a circular shape integrating interface with two flat panels and various equipments such as imaging devices and CBCT devices.

For example, an angular indicator as visual device is located on the back wall of patient enclosure. Said angular indicator shows the gantry angular position and is able to indicate the sense of the circular motion taken by the gantry. This angular indicator gives a mark to the practitioner when he is operating inside the patient enclosure, e.g. for patient positioning.

Preferably, the monitoring of patient positioning is performed by using cone beam computed tomography (CBCT).

Two CBCT devices are included preferably in an orthogonal manner within the patient enclosure in order to provide a view of the patient tumour for a good patient positioning.

For example, each CBCT device comprises an X-ray beam generator and a detector.

Advantageously, the first X-ray beam generator is included in the irradiation unit.

Advantageously, the second X-ray beam generator is arranged to emit an X-ray beam that has a direction perpendicular to the direction of the X-ray beam emitted by the first X-ray beam generator.

Preferably, imaging devices and more preferably CBCT detectors are located within the patient enclosure and aligned behind the patient bed or couch following the axis of their corresponding X-ray beam, and they may be maintained by an arm fixed on the back wall panel located on the vertical bottom of the patient enclosure, or maintained by rotating means located outside the patient enclosure.

Preferably, said telescopic arm 108 fixed on the gantry 109 is fixed beside said X-ray beam generator 107 at an angle of 90° from the axis of the hadron beam (FIG. 1a).

Preferably, the primary caterpillar's elongated member located in front of the X-ray beam generator 107 comprises a opening 106 to allow the passage of an X-ray beam.

Preferably, the axis of the telescopic arm 108 pulling the primary caterpillar 105 is perpendicular to the axis of the irradiation unit 110.

Consequently, for any angle taken by the irradiation unit 110, an X-ray beam is orthogonal to the X-ray beam coming from the X-ray beam generator included in the irradiation unit.

More preferably, the telescopic arm 108 comprises moving floor monitoring means which comprises a load cell arranged to check if the tensile strength between the caterpillar(s) and the gantry and/or between the caterpillar(s) and the telescopic arm does not exceed a predetermined value.

If the tensile strength exceeds a predetermined value, leading for example to the blocking of a caterpillar, the moving floor monitoring means sends the information for stopping the movement of the gantry in emergency to the gantry control means and the information of 'setting on' to the security means.

The present invention also provides a moving floor comprising the primary caterpillar 105 and the secondary caterpillar(s) 102, surrounding with the irradiation unit 110 a semi cylindrical room environment and forming a part of a patient enclosure 111 included in a rotating gantry 109 of a hadron therapy system.

The present invention can be adapted to any particle therapy apparatus using any type of ionizing radiations such as X-rays, gamma rays, electrons, hadrons, etc.

The moving floor provided by the present invention makes advantageously possible the free rotation of a radiation device, i.e. a irradiation unit supported by a rotating gantry, in a semi cylindrical patient enclosure having a horizontal floor segment and makes it advantageously possible to support an important charge permitting the access of a practitioner inside the patient enclosure for patient positioning without risk of chute, and this for any angle of irradiation. The design of this patient enclosure is safer and reduces fear from the patient since the patient does not see anymore the internal frame of the gantry and since no more gaps or weaker parts are present between the irradiation unit and the moving floor.

Accordingly, the apparatus according to the present invention avoids patient's vertigo or unsafe feeling when he/she is placed in the patient enclosure.

Furthermore, the apparatus according to the present invention is simpler since no motor or complicated anti-corotation devices combined with conveyor chains are required for the synchronization of the squirrel cage structure with the building fixed double rail.

In the present invention, the stiffness of the caterpillar's plates is responsible of the maintaining of the squirrel cage structure position on which is fixed the rear double rail, synchronized with the front double rail 301, (FIG. 3) attached to the building-fixed frame 201, the squirrel cage structure position sliding within the gantry by mean of wheels 205. Moreover, efficient security means as a buffer security means have been implemented around the irradiation unit 110 to avoid damage of the irradiation unit in case of blocking of a part of the hadron therapy system, the irradiation unit being one of the essential and expensive parts of particle therapy apparatus.

The present invention can also be described as follows:

The present invention aims to provide a hadron therapy system who does not have the drawbacks of prior art. In particular, it is an object of the invention to provide a hadron therapy system comprising a patient enclosure having a flat floor accessible and without gaps or weaker parts close to the nozzle for any irradiation angle.

It is a further object of the invention to provide, on such a hadron therapy system, some imaging devices.

Finally, It is a further object of the invention to provide a simpler hadron therapy system having a high safety level wherein minimal damage occurs in case of blocking of a part of the system.

In a first aspect, the present invention relates to a medical apparatus for hadron therapy comprising a rotating gantry provided by a beam support line guiding a beam produced by a hadron accelerator trough a nozzle towards a target (e.g. a tumor) located in a patient enclosure included in the rotating gantry, said patient enclosure having a semi-cylindrical shape and comprising the nozzle and a flexible moving floor, sandwiched between a building-fixed frame and a squirrel cage frame, said squirrel cage frame sliding within the gantry. The medical apparatus is characterised in that the moving floor comprises a primary caterpillar pulled mechanically and two secondary caterpillars fixed on both sides of the nozzle, the primary caterpillar and secondary caterpillars sliding into two double rails, one of said double rails being fixed on the squirrel cage frame an the other double rail being fixed on the building-fixed frame.

In a preferred embodiment of the invention, the nozzle is provided by two pairs of parallel rails disposed on both lateral sides of the nozzle, each of the parallel rails comprising a pivot which pulls the secondary caterpillars disposed on both sides of the nozzle.

Preferably, the double rails have a circle truncated form wherein the moving floor slides providing to the patient enclosure a horizontal floor.

More preferably, the primary caterpillar of the moving floor slides into internal rails of said double rails and said secondary caterpillars of the moving floor slide into external rails of said double rails.

According to the invention the secondary caterpillars fill a gap between the primary caterpillar and the nozzle.

In another embodiment of the invention, the medical apparatus for hadron therapy comprises a telescopic arm fixed on the gantry frame. Said telescopic arm pulls the primary caterpillar.

In an other embodiment of present invention, the caterpillars are an assembly of plates linked together, said plates being made in wood, plastic, glass fiber, a composite material, a metal such as iron, steel, aluminium, magnesium, titanium, copper, nickel, zinc or a combination hereof. Preferably, said plates are made in aluminium and provided by wheels on their extremities for rolling into the grooves of the double rails.

In an other embodiment of the invention, said caterpillar's plates have a sufficient rigidity, able to maintain the double rear rail which is fixed in the squirrel cage frame, in a fixed position and synchronized with the double front rail which is fixed on the building-fixed frame.

Preferably, an X-ray beam generator is fixed on the telescopic arm.

More preferably, said primary caterpillar has a hole located in front of the X-ray beam generator fixed on the telescopic arm.

In the medical apparatus for hadron therapy of the invention, the X-ray beam provided by said X-ray beam generator fixed on the telescopic arm is maintained orthogonal to an X-ray beam provided by an X-ray beam generator included in the nozzle.

In the medical apparatus for hadron therapy according to the invention, the rotating gantry is related to a gantry control system providing the information to stop in case of the blocking of a part of the whole system.

In the medical apparatus for hadron therapy according to the invention, the gantry continues to rotate until an angle of maximum 5° after the information of stopping provided by the gantry control system.

In the medical apparatus for hadron therapy according to the invention, the nozzle is provided by a buffer protection system able to set off in case of blocking of a part of the whole hadron therapy system.

In the medical apparatus for hadron therapy according to the invention, the buffer protection system is able to absorb a circular motion of the gantry of at least 5° to avoid damage on the nozzle.

In the medical apparatus for hadron therapy according to the invention, the telescopic arm is provided by a load cell monitoring the tensile strength of the primary caterpillar and providing stopping information to a gantry control system in case of reaching a predetermined traction value.

A medical hadron therapy system is described referring to FIGS. 1 and 2. It comprises a charged particle beam generating unit such as a cyclotron or a linac (not represented) and a gantry (109). A beam transport line guides the accelerated particle beam from the beam generating unit towards a target located in a patient enclosure included in a rotating gantry. The beam transport line is provided by deflecting means and has a curved part fitting with the gantry and able to rotate with the gantry.

FIGS. 1 *a* and *b* show a front view of a part of a hadron therapy system, comprising a gantry (109) (represented partially on FIG. 1 and FIG. 2). Said gantry is able to rotate around an axis of rotation D, said axis being perpendicular to the plane of the drawing. Said gantry is provided by a beam support line (not shown) guiding the beam produced by a hadron accelerator trough a nozzle (110) towards a target (e.g. a tumour) located in the patient enclosure (111, in hatched zone in FIG. 1 *b*) included in the gantry (109).

Patient enclosure (111) is a generic name including the nozzle (110) and all panels and/or covers that visually finish and close a room environment inside the gantry. Said panels and covers have esthetic and overall safety functionality. A patient bed or couch (not represented) may be positioned from the outside into the patient enclosure. Patient enclosure is designed to give a feeling of safety to the patient located inside this enclosure.

Patient enclosure (111), comprises a front double rail (301, FIG. 3) attached to a building-fixed frame (201) interfacing mechanically the treatment room. This double rail 301 may be called also the motionless building-fixed double rail. The patient enclosure (111) comprises further a rear double rail (302) fixed on a squirrel cage structure (202) and opposed to (i.e. facing) the front double rail. This squirrel cage structure (202) rolls within the gantry frame (109) by means of wheels (204, 205). Both double rails have a circle truncated form as represented on FIG. 3.

A continuous series of jointed plates makes a deformable surface called caterpillar which is sandwiched between the two double rails and slides, e.g. by means of wheels fixed on each plate. In an embodiment of the invention, three caterpillars are present, a primary caterpillar (105) and two secondary caterpillars (102). The primary caterpillar (105) and the two secondary caterpillars (102) slide into both double rails having a circle truncated form, providing a horizontal floor in the patient enclosure. In a preferred mode of realization of the invention, in a view from the inside of the patient enclosure (111), the secondary caterpillars (102) are located backwards of the primary caterpillar (105). Said secondary caterpillars (102) slide into the external rails (103) of rear and front double rails, while the primary caterpillar (105) slides into the internal rail (104) of rear and front double rails.

Said plates of the caterpillars are made in a rigid material such as wood, plastic, glass fiber, a composite material, a metal such as iron, steel, aluminium, magnesium, titanium, copper, nickel, zinc or a combination hereof. In a preferred embodiment of the invention, said caterpillars are made in aluminium.

Said primary caterpillar (105) is pulled by a telescopic arm (108) fixed on the gantry (109) and slides in synchrony with the gantry (109) into internal rails of both double rails. Said secondary caterpillars (102) slide into external rails of both double rails and are pulled mechanically by the nozzle (110). With such an arrangement and because of the rigidity of the caterpillar's plates, the position of the squirrel cage structure (202) on which is fixed the rear double rail (302) stays in the same position and synchronized with the motionless building-fixed double rail (302), while the gantry (109) rotates.

Furthermore, the nozzle (110) is provided by two pairs of parallel rails (101), each pair of parallel rails being disposed on both sides of the nozzle. A pivot, sliding into said parallel rails (101) of the nozzle (110), pulls the secondary caterpillars (102). Such a disposition provides a patient enclosure (111) having a safe rolling floor in which the nozzle (110) is able to rotate freely, able to support one person or more, even if the nozzle (110) is located in the bottom of patient enclosure (111) since no gaps or weaker part around the nozzle are present.

A security system is provided on the nozzle to avoid damage of said nozzle in case of blocking of one of the caterpillars or an other part of the whole hadron therapy system. The principle of said security system is shown on FIG. 4. In case of failure detected by a control system (i.e. switch system disposed along the double rails), the gantry is stopped and the security system is activated. Since the gantry is an imposing system having a certain inertia, it is not permitted to stop the gantry in an abrupt way under penalty of damaging the gantry. During the stopping phase, the gantry decelerates first, and then really stops after a circular motion of maximum 5°. In case of blocking of a caterpillar, said caterpillar may encounter the nozzle and damage it since caterpillar's plates are rigid. To absorb the impact between the nozzle and one or two caterpillars, a buffer system (401) having a parallelogram shape is located between the nozzle rails (101) and the nozzle (110) to avoid damage of the nozzle during the stopping phase. This buffer system acts as a shock absorber; the parallelogram buffer is crushed while the gantry decelerates. Such a buffer system is designed to absorb a circular motion of at least 5°. It is evident that the man skilled in the art could include such a buffer security system in any patient enclosure of a hadron therapy system, e.g. a hadron therapy system wherein the moving floor comprises a unique caterpillar. It could be also imagined that the security function of this buffer might be substituted by a mechanical function providing a means for the nozzle to rotate freely inside a patient enclosure having a truncated form. Moreover both functionalities of this buffer system might be exploited.

The vertical bottom of the squirrel cage, i.e. the vertical bottom of the patient enclosure, is terminated by a back wall panel which makes a circular shape integrating interfaces with two flat panels and various equipment items. In an embodiment of the invention, an angular indicator as visual device is located on the back wall of the patient enclosure. Said angular indicator shows the gantry angular position and is able to indicate the sense of the circular motion taken by the gantry. This angular indicator gives a mark to the practitioner when he is operating inside the patient enclosure, e.g. for patient positioning.

Generally, the monitoring of patient positioning is performed by cone beam computed tomography (CBCT). Two CBCT devices are included preferably in an orthogonal manner within the patient enclosure in order to provide a 3 dimensional view of the patient skeleton. CBCT devices comprise an X-ray beam generator and a detector. One of the X-ray beam generators is included in the nozzle while the second one is located within the gantry at an angle of preferably +/−90° from the first X-ray beam generator. Detectors are located within the patient enclosure and aligned backwards the patient following the axis of their corresponding X-ray beam. Detectors have to rotate in coordination with X-ray beam generators, and they may be fixed on the rolling floor; they may be maintained by an arm fixed on the back wall panel located on the vertical bottom of the patient enclosure, or maintained by rotating means located outside the patient enclosure.

In an embodiment of the invention, the telescopic arm (108) fixed on the gantry (109) is provided by (i.e. next to) an X-ray beam generator (107) which may be used in combination with a cone beam computed tomography detector. Preferably, said telescopic arm (108) is located at an angle of 90° from the axis of the hadron beam. A hole (106) is drilled in the primary caterpillar's plate located in front of the X-ray tube to ensure the pass of X-ray beam. The telescopic arm (108) maintaining the primary caterpillar (105) is fixed perpendicular to the nozzle (110), this configuration makes possible to have, for any angle taken by the nozzle, an X-ray beam orthogonal to the X-ray beam coming from the X-ray beam generator included in the nozzle.

In another embodiment of the invention, a load cell is provided on the telescopic arm 108 to check if the tensile strength is not too important. If the tensile strength exceeds a predetermined value, for example in case of blocking of a caterpillar, the control system stops the gantry in emergency.

This invention provides a moving floor comprising the primary caterpillar and the secondary caterpillars, surrounding with the nozzle a semi cylindrical room environment and forming a part of a patient enclosure included in a rotating gantry of a hadron therapy system. Present invention could be applied with the same profit to the radiation therapy systems based on the use of other type of radiations as X-rays and so on. A moving floor provided by the invention makes possible the free rotation of a radiation system, i.e. a nozzle supported by a rotating gantry, in a semi cylindrical patient enclosure having a horizontal floor segment and makes it possible to support an important charge permitting the access of a practitioner inside the patient enclosure for patient positioning without risk of chute, and this for any angle of irradiation. The design of such a patient enclosure is safer and reduces fear of the patient since the patient does not see anymore the internal frame of the gantry and since no more gaps or weaker part are present between the nozzle and the moving floor. This design avoids to the patient vertigo or unsafe feeling when he/she is placed in such a patient enclosure. Also, configuration of the invention is simpler since no motors or complicated anti-corotation systems combined with conveyor chains are required for the synchronization of the squirrel cage frame with the building fixed double rail. In the invention, the rigidity of the caterpillar's plates is responsible for the maintaining of the squirrel cage frame position on which is fixed the rear double rail, synchronized with the front double rail (302, FIG. 3) attached to the building-fixed frame (201), the squirrel cage frame position sliding within the gantry by means of wheels.

Moreover, efficient security means such as a parallelogram buffer security system has been implemented around the nozzle to avoid damage of the nozzle in case of blocking of a part of the hadron therapy system, the nozzle being one of the essential and expensive parts of this hadron therapy system.

The invention claimed is:

1. An apparatus for particle therapy in a treatment room, the apparatus comprising:
    an irradiation unit for emitting a particle beam,
    a gantry comprising the irradiation unit, said gantry being rotatable around an axis,
    a squirrel cage structure, located within and supported by said gantry so that it can rotate relative to said gantry around said axis,
    a frame arranged so as to be motionless,
    a moving floor comprising a plurality of elongated members flexibly connected to each other and forming a primary caterpillar,
    two moving floor guide units having a truncated circle shape, facing each other, attached to said squirrel cage structure and the motionless frame respectively, and each of the two moving floor guide units comprising at least a first rail, said first rail having a truncated circle shape,
    said primary caterpillar being slidably arranged on said first rail, and wherein each moving floor guide unit further comprises at least a second rail having a truncated circle shape and the moving floor further comprises at least one secondary caterpillar comprising elongated members flexibly connected to each other, said secondary caterpillar being slidably arranged on said second rail and attached to the irradiation unit so that it can rotate with the irradiation unit.

2. The apparatus for particle therapy according to claim 1, wherein a set of second rails is positioned externally relatively to the set of first rails.

3. The apparatus for particle therapy according to claim 1, wherein a set of second rails is positioned internally relatively to the set of first rails.

4. The apparatus for particle therapy according to claim 1, wherein said irradiation unit comprises two pairs of guiding units connected to said irradiation unit each secondary caterpillar comprising at least a pivot connected to the closest end of said caterpillar relatively to the irradiation unit and said pivots being arranged so as to slide into said guiding units.

5. The apparatus for particle therapy according to claim 1, further comprising a telescopic arm connected to both said gantry and said primary caterpillar.

6. The apparatus for particle therapy according claim 1, wherein said elongated members comprise wood, plastic, glass fiber, composite material, metal, or a combination thereof.

7. The apparatus for particle therapy according to claim 1, wherein said elongated members comprise aluminium.

8. The apparatus for particle therapy according to claim 1, wherein the irradiation unit further comprises a first X-ray beam generator.

9. The apparatus for particle therapy according to claim 8, further comprising a second X-ray beam generator connected to said gantry, located beside said telescopic arm, the directions of the X-ray beams delivered by the first and second X-ray beam generators being orthogonal.

10. The apparatus for particle therapy according to claim 1, further comprising a security component connected to the irradiation unit, to avoid damages to the apparatus.

11. The apparatus according to claim 10, wherein said irradiation unit comprises two pairs of guiding units connected to said irradiation unit, each secondary caterpillar comprising at least a pivot connected to the closest end of said caterpillar relatively to the irradiation unit and said pivots being arranged so as to slide into said guiding units, and wherein said guiding units are connected to the irradiation unit through a buffer component arranged between each guiding unit and the irradiation unit.

12. The apparatus according to claim 11, wherein said buffer component comprises piston and cylinder arrangements.

13. The apparatus for particle therapy according to claim 10, wherein said security component is configured to absorb a circular motion of the gantry of at least 5° for avoiding any damage to the irradiation unit.

14. The apparatus for particle therapy according to claim 10, further comprising a gantry controller configured to control the movements of the gantry, and further comprising a moving floor monitor configured to monitor the movements of the moving floor and to provide information to said gantry controller and to said security component, and wherein the security component is set on and/or set off according to information received from said moving floor monitor.

15. The apparatus for particle therapy according to claim 14, further comprising a telescopic arm connected to both said gantry and said primary caterpillar, and wherein the moving floor monitor comprises a load cell arranged on the telescopic arm configured to check if the tensile strength between the caterpillar(s) and the gantry and/or between the caterpillar(s) and the telescopic arm does not exceed a predetermined value.

16. The apparatus for particle therapy according to claim 1, wherein the frame is fixed to a wall of the treatment room.

17. The apparatus for particle therapy according to claim 6, wherein the metal is selected from the group consisting of iron, steel, aluminum, magnesium, titanium, copper, nickel, zinc, and combinations thereof.

* * * * *